(12) United States Patent
Aubry et al.

(10) Patent No.: US 11,408,322 B2
(45) Date of Patent: Aug. 9, 2022

(54) DETECTION SENSOR COMPRISING A SELECTIVE HIGH-ELECTRON-MOBILITY TRANSISTOR FOR DETECTING A GASEOUS OR LIQUID COMPONENT

(71) Applicants: PSA AUTOMOBILES SA, Velizy-Villacoublay (FR); GEORGIA TECH LORRAINE, Metz (FR); CENTRE NATIONAL DE LA RECHERCHE SCIENTIFIQUE, Paris (FR)

(72) Inventors: Vincent Aubry, Orsay (FR); Abdallah Ougazzaden, Marly (FR); Jean-Paul Salvestini, Metz (FR); Paul Voss, Metz (FR); Yacine Halfaya, Metz (FR); Chris Bishop, Metz (FR)

(73) Assignees: PSA AUTOMOBILES SA, Poissy (FR); GEORGIA TECH LORRAINE, Metz (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 615 days.

(21) Appl. No.: 16/341,022

(22) PCT Filed: Oct. 16, 2017

(86) PCT No.: PCT/EP2017/076377
§ 371 (c)(1),
(2) Date: Apr. 10, 2019

(87) PCT Pub. No.: WO2018/069553
PCT Pub. Date: Apr. 19, 2018

(65) Prior Publication Data
US 2020/0040798 A1 Feb. 6, 2020

(30) Foreign Application Priority Data

Oct. 13, 2016 (FR) ...................................... 1659879

(51) Int. Cl.
*F01N 11/00* (2006.01)
*H01L 29/778* (2006.01)
(Continued)

(52) U.S. Cl.
CPC ....... *F01N 11/007* (2013.01); *G01N 27/4141* (2013.01); *G01N 33/004* (2013.01);
(Continued)

(58) Field of Classification Search
None
See application file for complete search history.

(56) References Cited

U.S. PATENT DOCUMENTS 7,045,047 B2    5/2006  Nakae et al.
7,825,435 B2 *  11/2010 Machida ................ H03K 17/74
                                                257/195
(Continued)

FOREIGN PATENT DOCUMENTS

FR    2985813 A1    7/2013
JP    2011-94969 A  5/2011

OTHER PUBLICATIONS

French Search Report from French Patent Application No. 1659879, dated Apr. 19, 2017.
(Continued)

*Primary Examiner* — Daniel S Larkin
(74) *Attorney, Agent, or Firm* — Greer, Burns & Crain, Ltd (57) ABSTRACT

A method and a sensor for detecting or measuring at least one specific component among a plurality of components present in a gaseous or liquid mixture by a sensor having at least one capturing cell with a high-electron mobility transistor including a source and a drain with a grid inserted between the source and the drain, a voltage being applied between the source and the drain, and a current intensity in
(Continued)

the capturing cell being recorded. The voltage between the source and the drain is controlled, which varies the intensity of the current, the voltage being controlled according to a voltage model predetermined by experience in order to provide a profile with an intensity which is characteristic of said at least one specific component.

10 Claims, 6 Drawing Sheets

(51) Int. Cl.
 *G01N 33/00* (2006.01)
 *G01N 27/414* (2006.01)
(52) U.S. Cl.
 CPC ..... *G01N 33/0029* (2013.01); *G01N 33/0037* (2013.01); *G01N 33/0054* (2013.01); *H01L 29/778* (2013.01)

(56) References Cited

U.S. PATENT DOCUMENTS

2011/0045600 A1  2/2011  Ren et al.
2013/0288378 A1  10/2013  Gu et al.

OTHER PUBLICATIONS

International Search Report from International Patent Application No. PCT/EP2017/076377, dated Nov. 30, 2017.
Bishop et al., "Experimental Study and Device Design of NO, NO2, and NH3 Gas Detection for a Wide Dynamic and Large Temperature Range Using Pt/AlGaN/GaN HEMT", IEEE Sensors Journal (2016), 16(18), pp. 6828-6838.
Halfaya et al., "Investigation of the Performance of HEMT-Based NO, NO2 and NH3 Exhaust Gas Sensors for Automotive Antipollution Systems", Sensors (2016), 16(3), pp. 1-12.

* cited by examiner

DETECTION SENSOR COMPRISING A SELECTIVE HIGH-ELECTRON-MOBILITY TRANSISTOR FOR DETECTING A GASEOUS OR LIQUID COMPONENT

BACKGROUND

The invention relates to a sensor for detecting or measuring a specific component present in a gaseous or liquid mixture, the sensor comprising a collection cell having a high-electron-mobility transistor.

A high-electron-mobility transistor, also known by the acronym HEMT, comprises a source and a drain with a gate inserted between the source and the drain. The operation of the collection cell is based on the conductivity between two ohmic contacts which are the source and the drain, by the electrostatic action of a control electrode which is the gate.

Hereinafter, a preferential application of the sensor according to the present invention will be developed as a sensor for selectively detecting a polluting element present in the exhaust gases evacuated from an internal combustion engine by an exhaust line of a motor vehicle. This application is not limitative of the present invention.

It is known that the exhaust gases from vehicles contain numerous chemical components, some of which are toxic to the health of persons, and some to the environment. In order to limit these pollutants for the environment and health, regulations have been introduced in Europe, the United States and Japan for the measurement and/or the detection of these chemical components.

With regard to the nitrogen oxides forming part of these dangerous chemical components, hereinafter denoted by their chemical formula $NO_x$, the emission limits will become increasingly strict, and will probably be specific to the different nitrogen oxides, including $NO$, $NO_2$, $N_2O$, etc., whereas $NO_x$ are currently regulated overall.

The sensors currently used for vehicle exhaust gases are $NO_x$ sensors and $O_2$ probes, also known as lambda probes. They are based on the operation principle of solid electrolytes and Nernst's law, and are based on yttrium-doped zirconium oxide.

These $NO_x$ sensors are not selective between the different gases and detect an overall concentration corresponding to the gases $NO_2$, $NO$, $N_2O$, $NH_3$. In addition, their response time is high and these sensors are relatively expensive.

Other different gas sensor technologies exist, such as optical sensors, metal oxide sensors, acoustic sensors, gravity sensors, etc. But, currently, there are no sensitive, rapid, low-cost sensors that are resistant to a vehicle exhaust system environment in and selective of the different gaseous species such as $O_2$, $H_2$, $NO_2$, $NO$, $N_2O$, $CO$, $CO_2$.

A new generation of sensors that are selective between gases is therefore necessary in order to comply with this development in the regulations. In addition, a sensor making it possible to determine separately the concentration of ammonia or $NH_3$ and the $NO/NO_2$ ratio would make it possible to improve the regulation of a selective catalytic reduction system, also known by the abbreviation SCR, reducing the $NO_x$ by injection of $NH_3$ resulting from the decomposition of a reducing agent initially in the form of a urea-based mixture.

In this context, work has been carried out with respect to the development of gas sensors based on nitride (III-N) semiconductors. Semiconductors based on III-N materials are materials with a wide forbidden band, which makes them of interest for gas sensor applications. Their thermal stability and their high breakdown voltage make them suitable for high-temperature applications, which is the case for example for exhaust lines and/or internal combustion engines for motor vehicles.

Such measurement of exhaust gases using sensors brings essential advantages. In fact, the environment of exhaust gases is highly stressed in view of the high temperatures encountered.

Removing the electrical contacts makes it possible to avoid the cost constraints associated with the necessary connectors. In addition, the performance of these connectors in the high-temperature environment can be the limiting factor in terms of temperature and not the capability of the sensor itself.

Sensors can also operate in liquid environments or those that are difficult to access and can also make it possible to measure liquid contents. This also makes it possible to reduce the bulk of the sensors, which no longer require connectors.

However, the sensors for measuring and/or detecting a component within a liquid or a gaseous mixture can be improved, in particular with respect to the selectivity of the component to be detected, which needs to relate to this component alone.

Document US 2013/0288378 A1 discloses a sensor or sensors used for detecting and measuring one or more components in a chemical environment. This sensor or sensors are based on a semiconductor structure comprising an interfacial region containing a two-dimensional electron gas. A catalyst, reacting with the component(s) is brought into contact with the semiconductor structure. Particles stripped from the component or components by the catalyst passivate the surface of the semiconductor structure at the interface between the catalyst and the structure, causing a change in charge density in the gas in the vicinity of the catalyst.

When this base structure is incorporated into an electronic device, such as a high-electron-mobility transistor or a Schottky diode, the change in charge density manifests into a change in an electrical response of the device. For example, in a high-electron-mobility transistor, the change in charge density manifests in the form of a change in current through the transistor, and, in a Schottky diode, the change in charge density manifests in the form of a change in capacitance. On the other hand, this document does not disclose or suggest how it would be possible to specifically detect a component by means of such a device.

SUMMARY

Consequently, the problem that forms the basis of the present invention is, for a sensor for detecting and/or measuring a component contained in a gaseous or liquid mixture, the sensor comprising a collection cell having a high-electron-mobility transistor, to accurately detect and/or measure this component content selectively with respect to the other different components that are present in the gaseous or liquid mixture.

In order to achieve this objective, a method of detecting or measuring at least one specific component from among several components present in a gaseous or liquid mixture is provided according to the invention by a sensor comprising at least one collection cell having a high-electron-mobility transistor comprising a source and a drain with a gate inserted between the source and the drain, a drain-to-source voltage being applied and a current intensity in the collection cell being recorded, characterized in that the drain-to-source voltage is driven, which varies the current intensity, the voltage being driven according to a voltage model predetermined by experiment in order to deliver a profile with an intensity characteristic of said at least one specific component.

The technical effect is to obtain a sensor or an assembly of sensors making it possible, by different drain-to-source voltages, to greatly improve the selectivity to a specific component to be detected. The method according to the invention is very advantageous compared to the current methods, in particular the cycle at temperature which requires much longer response times.

By using a method according to the present invention, the selectivity can be achieved in less than one second simply by controlling multiple sensors by means of different drain-to-source voltages, or simply by driving this voltage on a single sensor. This control makes it possible to obtain sensors or an array of sensors having a high-electron-mobility transistor that are selective and very rapid in detecting gases or liquids and measuring gas or liquids, in particular for applications measuring and controlling exhaust gases.

The advantages of the solution are a selectivity between the different components, an improved response time and a reduced cost.

Advantageously, the intensity profile characteristic of said at least one specific component has inversion of the sign of the current intensity in the sensor.

Advantageously, the same transistor of the sensor is subject consecutively to different predetermined models dedicated to different specific components.

Advantageously, the predetermined voltage model is on a high-frequency voltage scale.

Advantageously, the components detected or measured are taken, individually or in combination, from among nitrogen monoxide, nitrogen dioxide, ammonia, carbon monoxide, carbon dioxide and oxygen, these components being contained in the gases evacuated by means of an exhaust line of a motor vehicle.

The invention also relates to a method for cleaning a sensor comprising at least one collection cell having a high-electron-mobility transistor comprising a source and a drain with a gate inserted between the source and the drain, the sensor operating according to such a method for detecting or measuring at least one specific component from among several components present in a gaseous or liquid mixture, characterized in that a polarization voltage is applied between at least two of the elements from among the source, the drain and the gate or by an electrode inserted successively between two of the elements from among the source, the drain and the gate, the polarization voltage or the voltage of the electrode being predetermined in order to release the ions from said at least one specific component retained on the gate of the sensor.

The application of a voltage increases the temperature of the sensitive area, causing the release of the gas ions captured by the sensitive area. This surface release, by breaking the bonds, regenerates the sensor to its initial situation. Typically, the sensors having a high-electron-mobility transistor require a temperature increase of 300° C. in order to regenerate. By applying a voltage to a weak area, for example the gate, this local temperature increase is sufficient without increasing the temperature of the sensor as a whole.

This novel method allows rapid, targeted regeneration of the sensor in the case of an array of sensors allowing regeneration of certain sensors while others continue to operate, ensuring continuous measurement of the gases.

The invention relates to a sensor for detecting or measuring at least one specific component from among several components present in a gaseous or liquid mixture, the sensor comprising at least one collection cell having a high-electron-mobility transistor comprising a source and a drain with a gate inserted between the source and the drain, the sensor comprising a microprocessor with means for applying a source-to-drain voltage and means for monitoring the current intensity in the collection cell, characterized in that the microprocessor is equipped with means for driving the voltage according to a voltage model saved by storage means, means for recording the current intensity during application of the voltage model and means for recognizing an intensity profile characteristic of said at least one specific component saved by the storage means.

Advantageously, the sensor comprises means for applying a regeneration voltage between at least two of the elements from among the source, the drain and the gate or an electrode in the form of successive slots extending successively between two of the elements from among the source, the drain and the gate and means for applying a regeneration voltage to the electrode, the regeneration voltage being sufficient to carry out regeneration of a sensor by release of ions retained by the sensor from said at least one specific component.

The invention relates to an assembly of at least two detection or measuring sensors, each sensor detecting a respective specific component present in a gaseous or liquid mixture, characterized in that said at least two sensors are as described previously, each of said at least two sensors having a stored voltage drive model and a stored intensity profile characteristic of said at least one specific component, selective detection of a respective component being made by each of said at least two sensors.

The invention relates to an exhaust line of a motor vehicle internal combustion engine, characterized in that it comprises such a sensor or such an assembly of at least two detection or measurement sensors, the gaseous or liquid mixture being formed by exhaust gases passing through the exhaust line and said at least one specific component or said at least two specific components being respectively one or more pollutants contained in the exhaust gas.

BRIEF DESCRIPTION OF THE DRAWINGS

Other characteristics, aims and advantages of the present invention will become apparent on reading the following detailed description and in the light of the attached drawings given by way of non-limitative examples in which.

DETAILED DESCRIPTION

It should be borne in mind that the Figures are given by way of example and are not limitative of the invention. They constitute diagrammatic representations intended to facilitate understanding of the invention and are not necessarily on the scale of practical applications. In particular, the dimensions of the different elements shown are not representative of reality.

Hereinafter, reference is made to all the figures in combination. When reference is made to one or more specific figure(s), these figures are taken in combination with the other figures in order to recognize the numerical references denoted.

Figure 1:
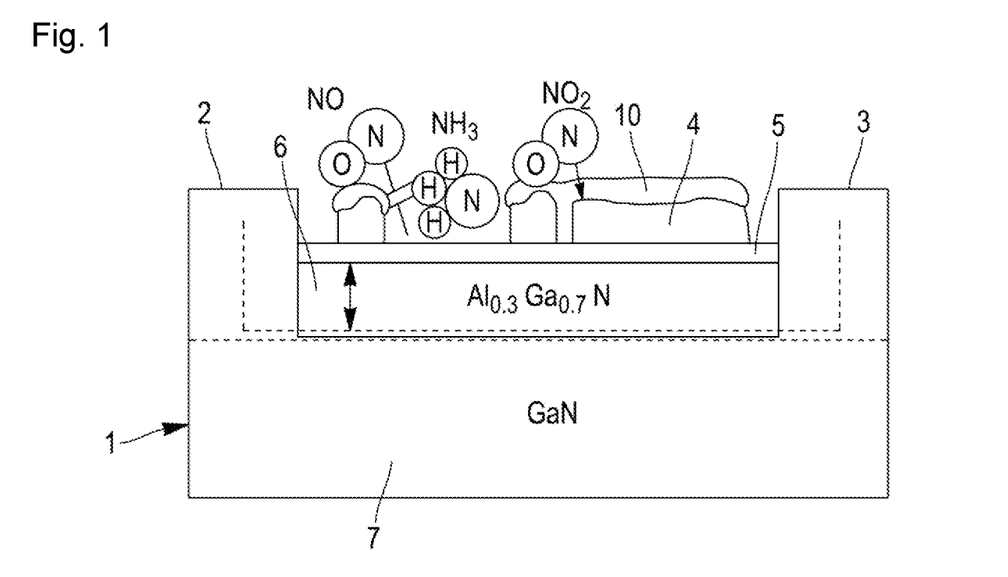
FIG. 1 is a diagrammatic representation of an embodiment of a sensor according to the present invention, the sensor having a collection cell comprising a high-electron-mobility transistor.

With reference to all of the figures and in particular FIG. 1, the present invention relates to a sensor 1 for detecting or measuring at least one specific component present in a gaseous or liquid mixture. The sensor 1 comprises at least one collection cell having a high-electron-mobility transistor comprising a source 2 and a drain 3 with a gate 4 inserted between the source 2 and the drain 3.

A high-electron-mobility transistor supports the drain 3 and the source 2 at two opposite lateral ends. In an embodiment, between the source 2 and the drain 3 extends a nanostructured III-N semiconductive layer 5 and a layer of $Al_{0.3}G_{0.7}N$ 6 or an active electrostatic interaction layer, the semiconductive layer 5 being superimposed on the layer of $Al_{0.3}Ga_{0.7}N$ 6. The layer of $Al_{0.3}Ga_{0.7}N$ 6 is superimposed on a layer of GaN 7.

The nanostructured III-N semiconductive layer 5 supports a layer 4 or layers forming an input gate for the ions of the component(s) to be detected or measured, for example dissociated oxygen negative ions $O^{2-}$ for nitrogen oxides $NO_x$ or oxygen $O_2$, creating a potential difference. This layer 4 or these layers forming an input gate, advantageously coated with a layer of oxides 10, can be platinum or tungsten.

Figure 5:
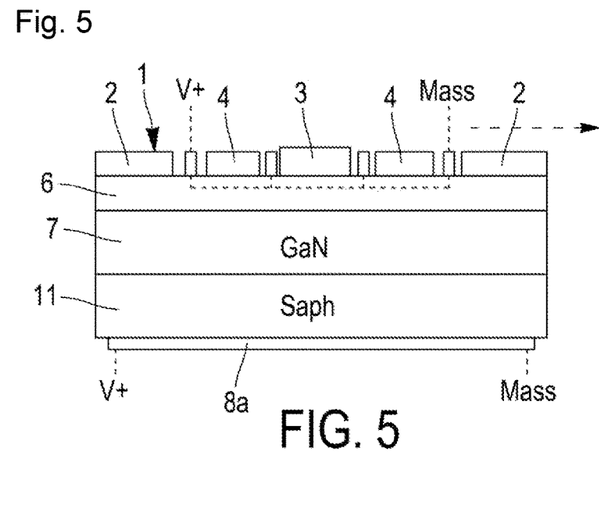
FIGS. 5 and 5a show preferential regeneration, in the context of the present invention, of an effective area of the sensor using a regeneration electrode.

Under the layer $Al_{0.3}G_{0.7}N$ 6 a channel extends connecting the source 2 and the drain 3, the channel itself being superimposed on a layer of GaN 7, acting as an insulating substrate. In FIG. 5, a layer of sapphire 11 is provided below the layer of GaN 7.

The sensor 1 comprises a microprocessor with means for applying a voltage between the source 2 and the drain 3 and means for monitoring the current intensity Imeas in the collection cell. According to the present invention, the microprocessor is equipped with voltage drive means according to a voltage model saved by storage means, means for recording the current intensity Imeas during application of the voltage model and means for recognizing an intensity profile characteristic of said at least one specific component saved by the storage means.

The present invention also relates to a method for detecting or measuring at least one specific component from among several components present in a gaseous or liquid mixture by means of a sensor 1 as previously described. A voltage is applied between the source 2 and the drain 3 and a current intensity Imeas in the collection cell is recorded.

According to the invention, a source 2-to-drain-3 voltage is driven, varying the current intensity Imeas, the voltage being driven according to a voltage model predetermined by experiment in order to deliver an intensity profile characteristic of said at least one specific component.

The same transistor of the sensor 1 can be subjected consecutively to different predetermined models dedicated to different specific components; this therefore by changing the voltages applied between the source 2 and the drain 3, voltages which were the subject of the predetermined production of a voltage model. This predetermined voltage model can be on a high-frequency voltage scale.

A preferential, but non-limitative, application of the present invention is for detecting or measuring the following components, taken individually or in combination: nitrogen monoxide NO, nitrogen dioxide $NO_2$, ammonia $NH_3$, carbon monoxide CO, carbon dioxide $CO_2$ and oxygen $O_2$. These components are non-limitative and are the main contents in the gases evacuated by means of an exhaust line of a motor vehicle.

Figure 2:
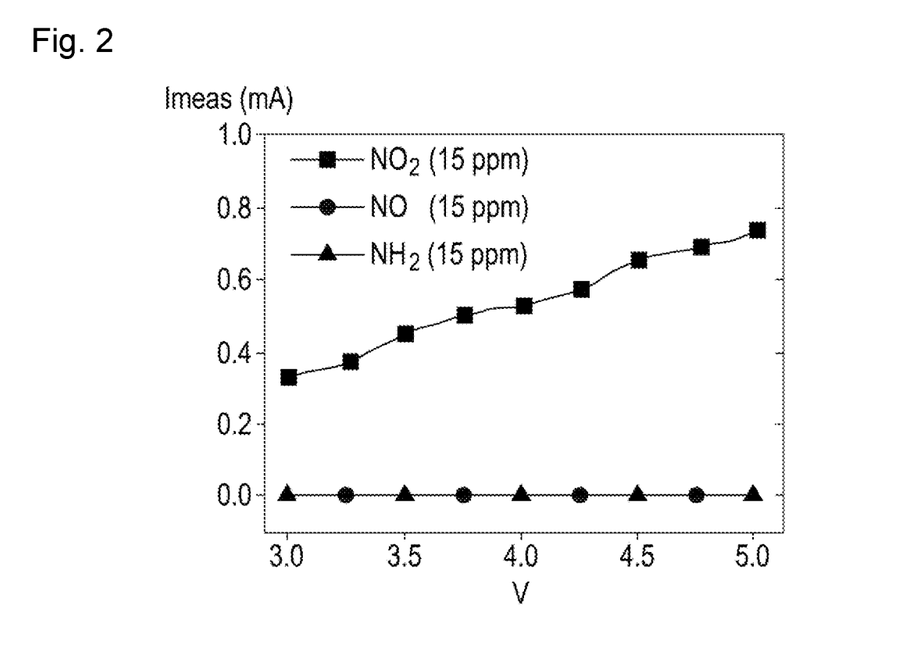
FIG. 2 shows current intensity curves as a function of the voltage for different components such as nitrogen monoxide NO, nitrogen dioxide $NO_2$ and ammonia $NH_3$.

FIG. 2 shows current intensity Imeas curves in milliamperes as a function of the voltage in volts for different components such as nitrogen oxide NO, nitrogen dioxide $NO_2$ and ammonia $NH_3$, for 15 ppm and a temperature of 300° C.

The intensity profile characteristic of said at least one specific component can have an inversion of sign of the current intensity Imeas in the sensor 1. This is for example the case for the detection of a gaseous component in the exhaust line of a motor vehicle which is nitrogen monoxide or NO. The signal current for NO changes direction in the structure of the sensor 1 having a high-electron-mobility transistor but this signal change takes place only in the presence of NO and not of nitrogen dioxide $NO_2$ or ammonia $NH_3$.

Figure 3:
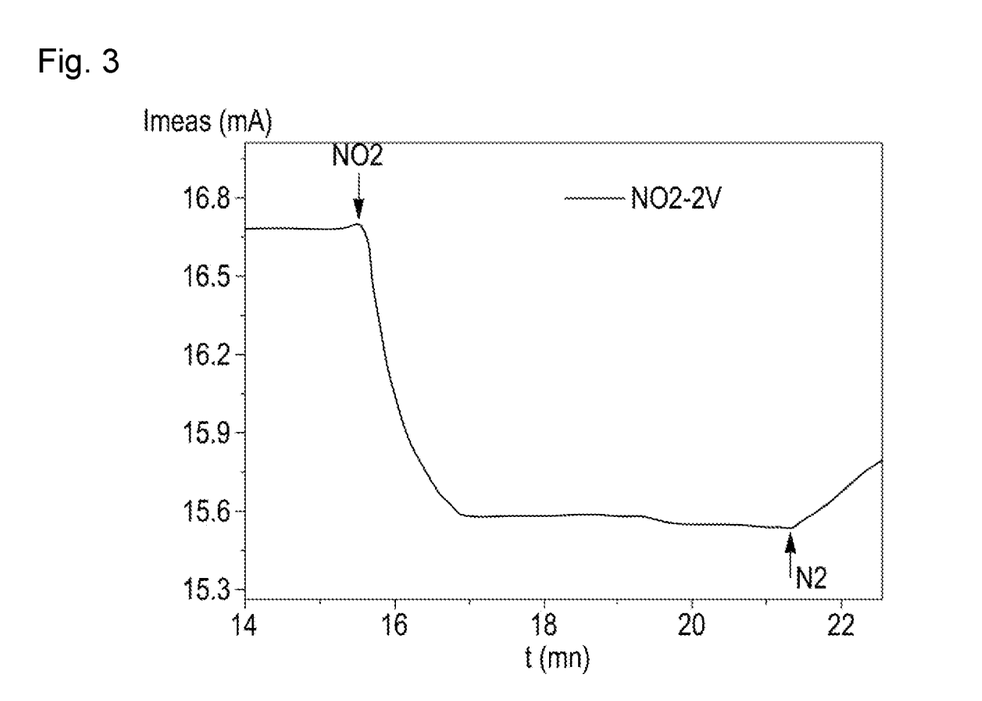
FIGS. 3 and 3a show, respectively for voltages of 2 Volts and 7 Volts as a function of time, the measured voltage for detecting nitrogen dioxide.
Figure 3A:
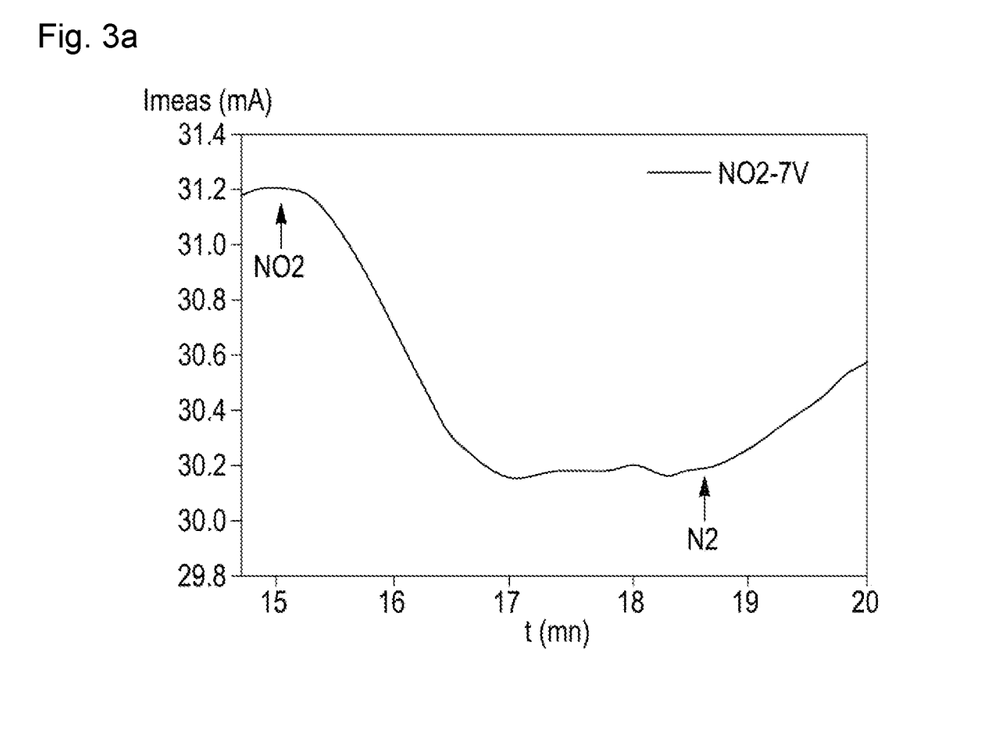

FIGS. 3 and 3a show, respectively for voltages of 2 Volts and 7 Volts, the current measured in milliamperes mA for detecting nitrogen dioxide $NO_2$ as a function of time tin minutes. These FIGS. 3 and 3a are to be compared to FIGS. 4a, 4b and 4c relative to the current measured in milliamperes mA for detecting nitrogen monoxide NO when the sensor is subjected to nitrogen monoxide, as a function of time t in minutes, for different voltages respectively of 2, 5 and 7 Volts, the greatest variation in the current being in the form of a sudden fall occurring for 2 Volts. It can be seen that the evolution for nitrogen monoxide NO, unlike the case of the sensor in the presence of $NO_2$ in FIG. 3 or 3a greatly depends on the polarization voltage. An inversion of the evolution passing from a fall to a rise is observed when the polarization passes from 2 to 7 Volts.

Figure 4A:
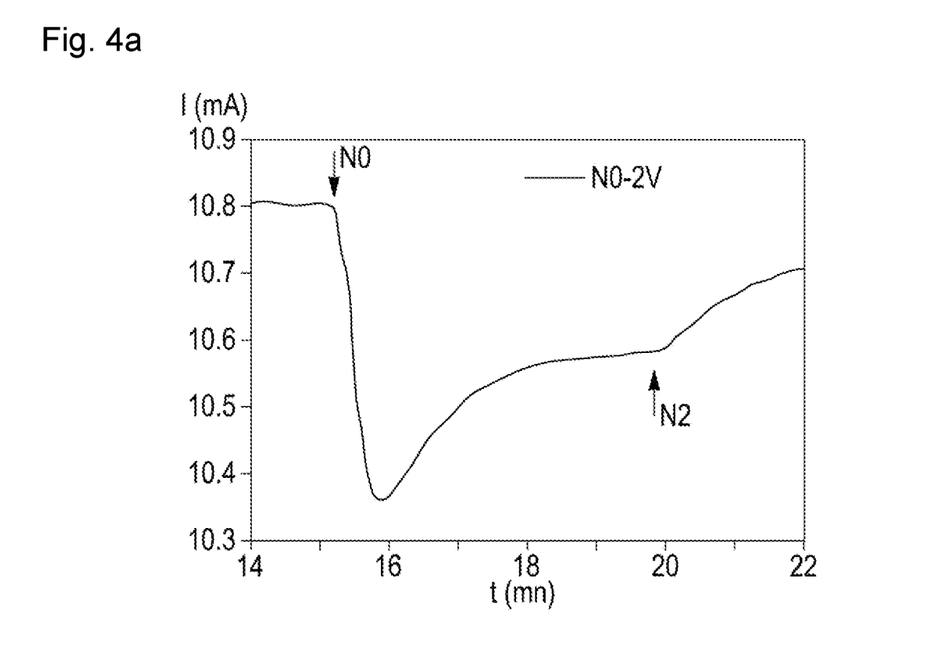
FIGS. 4a, 4b and 4c show current curves in milliamperes as a function of response time in minutes to nitrogen monoxide for different voltages of 2, 5 and 7 Volts respectively.
Figure 4B:
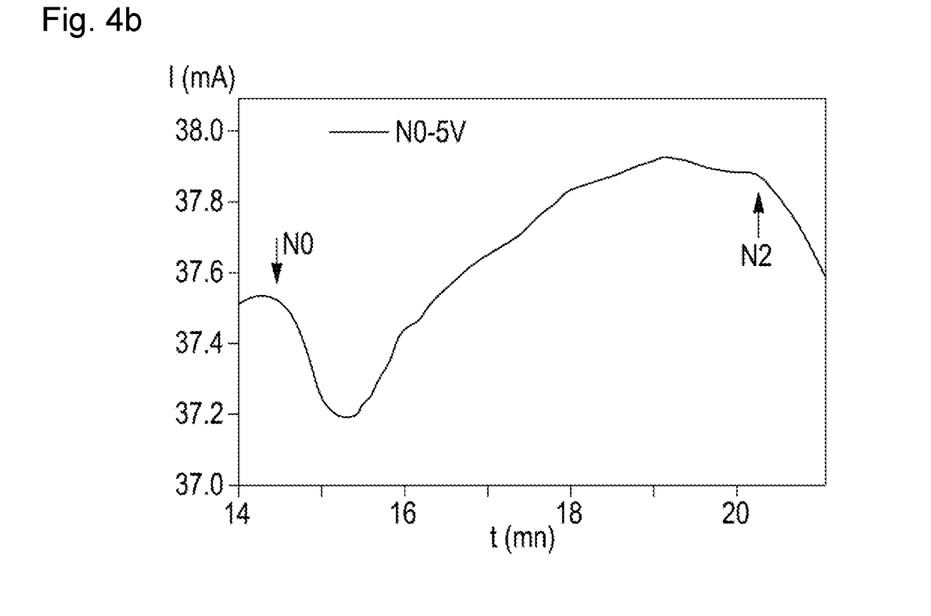
Figure 4C:
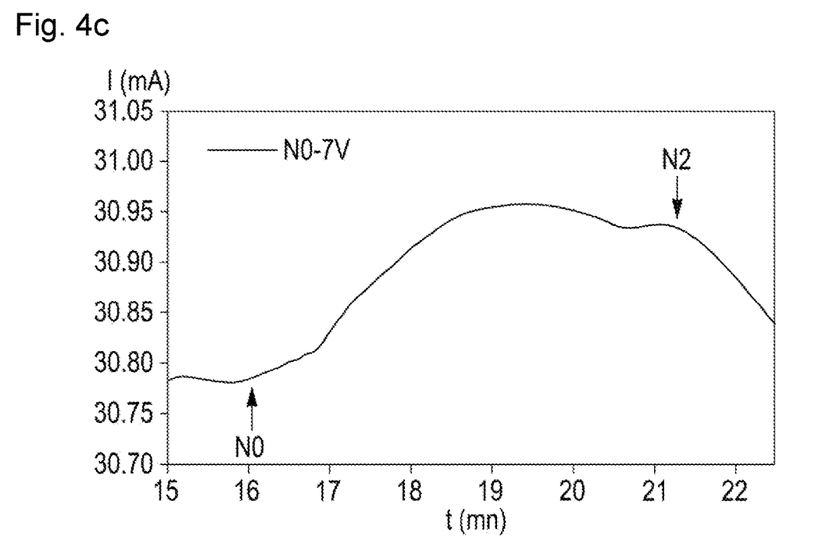

The change of sign of the NO signal is thus obtained by applying different voltages between the drain 3, source 2 and also the gate 4. This makes it possible to change the reaction of the chemical surface. It was established that a voltage model can be produced for various components specifically at a component taken individually and that the production of such a model can lead to accurate detection and measurement of the component by increasing the current intensity in the sensor 1.

It is possible to use the sign changes of the NO signal in order to improve the selectivity of the sensors 1 to the different gases present, for example $NO_2$, $NH_3$, CO, $CO_2$, $O_2$ etc, in the case of the components in exhaust gases of a motor vehicle.

The invention also relates to an assembly of at least two detection or measuring sensors 1. Each sensor 1 detects a respective specific component present in a gaseous or liquid mixture. The two sensors 1 can be as previously described, each of said at least two sensors 1 having a stored drive voltage model and a stored intensity profile characteristic of said at least one specific component, a selective detection of a respective component being made by each of said at least two sensors 1.

Such a sensor 1 has the disadvantage of becoming fouled by the deposition of particles of components on its contact surface and in particular on the gate 4 thereof or on the layer of oxides 10 covering the gate 4. In the context of the method previously described for detecting or measuring at least one specific component from among several components present in a gaseous or liquid mixture, a method of cleaning the sensor 1 having a high-electron-mobility transistor can be implemented.

According to a first embodiment of the regeneration process according to the invention, a polarization voltage is applied by means of an electrode 9 inserted successively between two of the elements from among the source 2, the drain 3 and the gate 4, the voltage of the electrode 9 being predetermined in order to release the ions of said at least one specific component retained on the gate 4 by the sensor 1. This is shown in FIGS. 5 and 5*a* for an electrode 9.

According to a second embodiment of the regeneration process according to the invention, a polarization voltage is applied between two of the elements from among the source 2, the drain 3 and the gate 4, the polarization voltage being predetermined in order to release the ions of said at least one specific component retained by the sensor 1. This is shown in FIG. 6.

Figure 5A:
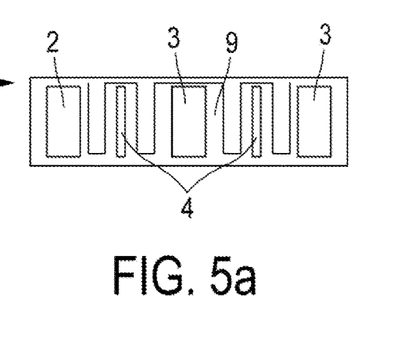
Figure 6:
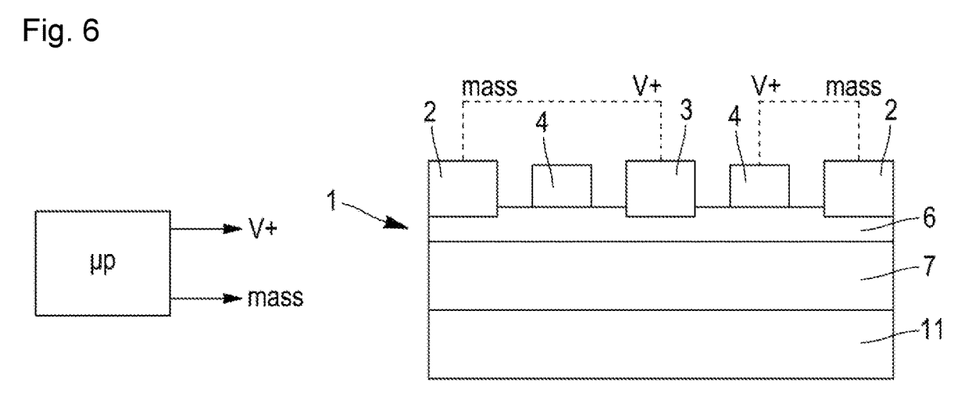
FIG. 6 shows preferential regeneration, in the context of the present invention, of the effective area of the sensor alternative to that in FIGS. 5 and 5a, the regeneration being produced by regeneration voltage.

In FIGS. 5, 5*a* and 6, V+ and Mass indicate the poles of the regeneration circuit. There can be an auxiliary regeneration circuit 8*a* at the base of the sensor 1.

With reference in particular to FIG. 1, the gate 4 comprises a body made from platinum or tungsten advantageously coated with a layer of oxides 10. A sensor 1 having a high-electron-mobility transistor can have numerous different detection mechanisms which are a function of the thickness of the gate 4, of its material and its morphology.

For example, the curves in FIG. 2 showing a selectivity between $NO_2$ and $NO/NH_3$ have been obtained using a fine platinum layer on BGaN/GaN contacts of a Schottky diode sensor.

The thickness of the platinum layer forming gate 4 can be 100 ηm in order to eliminate the presence of pores in the platinum layer, when grains form during the growth process of the BGaN surface. The thickness of the layer of the gate 4 has a significant impact on the sensitivity, 0% for 100 ηm of platinum layer for NO, $NO_2$, $NH_3$, compared with 20% for 15 ηm of platinum layer.

It has also been noted that the measurement signal due to the presence of $NH_3$ or $NH_3$ signal can be inverted by changing the sign and implementing changes to the morphology and thickness of the gate 4.

Figure 7:
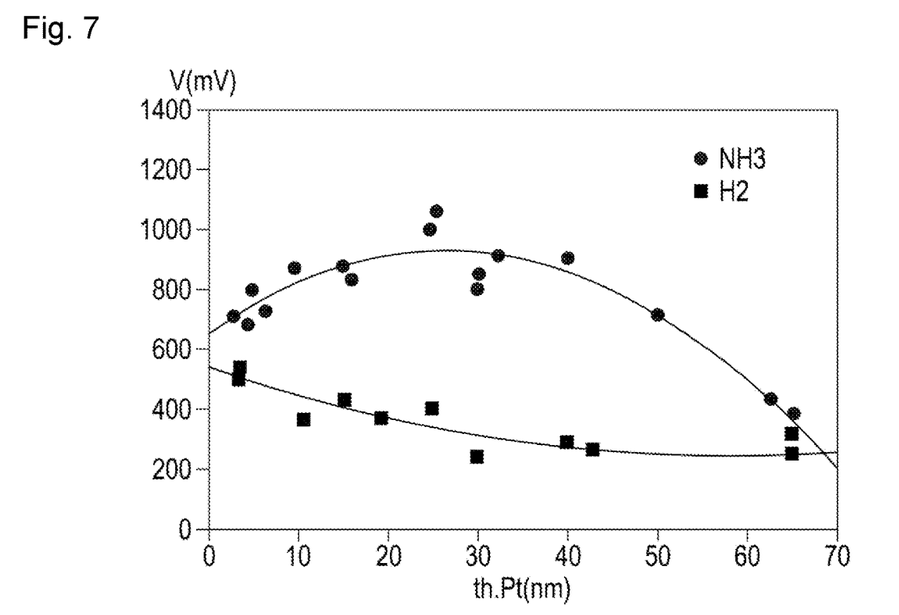
FIG. 7 shows two voltage curves obtained as a function of the thickness of the platinum layer of the gate of a sensor according to the present invention for a component in the form of hydrogen and ammonia, the voltage being representative of the sensitivity of the sensor with respect to these two elements.

FIG. 7 shows two voltage curves in millivolts mV with respect to a thickness of the platinum layer of a gate 4 in nanometres ηm for hydrogen H2 and ammonia $NH_3$ at 150° C. with 20% oxygen in argon as carrier gas. As the sensitivity of the sensor is a function of the voltage, it can be seen in FIG. 7 that the sensitivity is dependent on the thickness of the gate 4.

Figure 8:
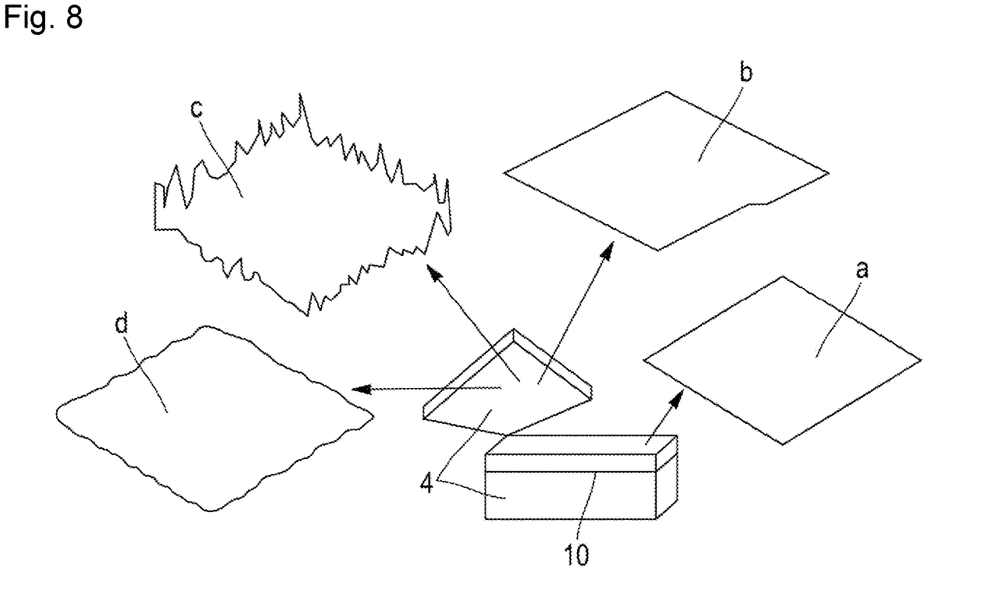
FIG. 8 shows several morphologies of the platinum layer forming a gate in a sensor according to the present invention.

FIG. 8 shows a different morphology of the gate 4 according to the method for producing the gate 4. The gate 4 in the form of a platinum layer can be obtained by evaporation referenced d in FIG. 8, by spraying at a first pressure referenced b, by spraying at a second pressure referenced c or coated with a layer of oxides referenced a with deposition of platinum by masking in nanopillars or other geometric structures.

These modifications can be applied to all of the structures of sensors 1 having a high-electron-mobility transistor or to the gate 4 in the form of a Schottky diode in order to improve the sensitivity and the selectivity.

The invention is in no way limited to the embodiments described and illustrated, which have been given merely by way of example.

The invention claimed is:

1. A method of detecting or measuring at least one specific component from among several components present in a gaseous or liquid mixture by means of a sensor comprising at least one collection cell having a high-electron-mobility transistor comprising a source and a drain with a gate inserted between source and drain, comprising: a drain-to-source voltage being applied; a current intensity (Imeas) in the collection cell being recorded; the source-to-drain voltage is driven; and varying the current intensity (Imeas), the voltage being driven for different voltages according to a voltage model predetermined by experiment in order to deliver a profile with an intensity which is characteristic of said at least one specific component.

2. The method according to claim 1, wherein the profile with an intensity which is characteristic of said at least one specific component has an inversion of sign of the current intensity (Imeas) in the sensor.

3. The method according to claim 1, wherein a same transistor of the sensor is consecutively subject to different predetermined models dedicated to different specific components.

4. The method according to claim 1, wherein the predetermined voltage model is on a frequency voltage scale.

5. The method according to claim 1, wherein the components detected or measured are taken, individually or in combination, from among nitrogen monoxide, nitrogen dioxide, ammonia, carbon monoxide, carbon dioxide and oxygen, these components being contained in the gases evacuated by means of an exhaust line of a motor vehicle.

6. The method for cleaning a sensor comprising at least one collection cell having a high-electron-mobility transistor comprising a source and a drain with a gate inserted between the source and the drain, the sensor operating according to a method for detecting or measuring at least one component specific to several components present in a gaseous or liquid mixture, according to claim 1, wherein a polarization voltage is applied between at least two of the elements between the source, the drain and the gate or by an electrode inserted successively between two of the elements from among the source, the drain and the gate, the polarization voltage or the voltage of the electrode being predetermined in order to release the ions of said at least one specific component retained on the gate of the sensor.

7. A sensor for detecting or measuring at least one specific component from among several components present in a gaseous or liquid mixture, the sensor comprising: at least one collection cell having a high-electron-mobility transistor comprising a source and a drain with a gate inserted between the source and the drain; the sensor comprising a microprocessor with means for applying a voltage between the source and the drain; means for monitoring the current intensity (Imeas) in the collection cell; the microprocessor is equipped with voltage drive means according to a voltage model for different voltages saved by storage means; means for recording the current intensity (Imeas) during application of the voltage model; and means for recognizing an intensity profile characteristic of said at least one specific component saved by the storage means.

8. The sensor according to claim 7, further comprising means for imposing a regeneration voltage between at least two of the elements from among the source, the drain and the gate or an electrode in the shape of successive slots extending successively between two of the elements from among the source, the drain and the gate and means for imposing a regeneration voltage to the electrode, the regeneration voltage being sufficient to regenerate the sensor by releasing ions of said at least one specific component retained by the sensor.

9. An assembly of at least two detection or measuring sensors, each sensor detecting a respective specific component present in a gaseous or liquid mixture, said at least two sensors are according to claim 7, each of said at least two sensors having a stored voltage drive model and a stored intensity profile which is characteristic of said at least one specific component, a selective detection of a respective component being made by each of said at least two sensors.

10. An exhaust line of an internal combustion engine of a motor vehicle, further comprising at least one sensor according to claim 7, or at least an assembly of at least two detection or measurement sensors, the gaseous or liquid mixture being formed by exhaust gases passing through the exhaust line and said at least one specific component or said at least two specific components being respectively one or more pollutants contained in the exhaust gas.

* * * * *